(12) United States Patent
Kawata et al.

(10) Patent No.: US 11,686,865 B2
(45) Date of Patent: Jun. 27, 2023

(54) RADIATION DETECTOR

(71) Applicant: CANON MEDICAL SYSTEMS CORPORATION, Tochigi (JP)

(72) Inventors: Go Kawata, Moriya (JP); Tatsuo Osaka, Nasushiobara (JP)

(73) Assignee: CANON MEDICAL SYSTEMS CORPORATION, Tochigi (JP)

( * ) Notice: Subject to any disclaimer, the term of this patent is extended or adjusted under 35 U.S.C. 154(b) by 36 days.

(21) Appl. No.: 17/454,107

(22) Filed: Nov. 9, 2021

(65) Prior Publication Data
US 2022/0146695 A1 May 12, 2022

(30) Foreign Application Priority Data
Nov. 11, 2020 (JP) .................................. 2020-187732

(51) Int. Cl.
*G01T 1/20* (2006.01)
*A61B 6/00* (2006.01)
*A61B 6/03* (2006.01)

(52) U.S. Cl.
CPC ............ *G01T 1/2018* (2013.01); *A61B 6/032* (2013.01); *A61B 6/4241* (2013.01)

(58) Field of Classification Search
None
See application file for complete search history.

(56) References Cited

U.S. PATENT DOCUMENTS

| | | | |
|---|---|---|---|
| 11,207,037 B2* | 12/2021 | Kawata | A61B 6/587 |
| 2008/0310585 A1* | 12/2008 | Ikhlef | H04N 5/32 |
| | | | 378/19 |
| 2010/0219345 A1* | 9/2010 | Franch | G01T 1/2985 |
| | | | 250/362 |
| 2020/0367836 A1* | 11/2020 | Kawata | A61B 6/4291 |

FOREIGN PATENT DOCUMENTS

JP 2013-190310 A 9/2013

* cited by examiner

*Primary Examiner* — Edwin C Gunberg
(74) *Attorney, Agent, or Firm* — Oblon, McClelland, Maier & Neustadt, L.L.P.

(57) ABSTRACT

A radiation detector according to an embodiment includes a scintillator array, a sensor array, electronic circuitry, a switch, and control circuitry. The scintillator array includes a plurality of scintillator pixels each configured to convert radiation into light. The sensor array includes a plurality of detection elements each configured to detect the light. The electronic circuitry is configured to output digital data on the basis of signals output from the detection elements. The switch is provided between the sensor array and the electronic circuitry. The control circuitry is configured to control the switch on the basis of a positional relation between the sensor array and the scintillator array.

12 Claims, 8 Drawing Sheets

RADIATION DETECTOR

CROSS-REFERENCE TO RELATED APPLICATIONS

This application is based upon and claims the benefit of priority from Japanese Patent Application No. 2020-187732, filed on Nov. 11, 2020; the entire contents of which are incorporated herein by reference.

FIELD

Embodiments described herein relate generally to a radiation detector.

BACKGROUND

Conventionally, medical image diagnostic devices each utilizing radiation to generate a medical image of a subject are known, such as X-ray computed tomography (CT) devices, positron emission tomography (PET) devices, single photon emission computed tomography (SPECT) devices, and gamma cameras. Such a medical image diagnostic device includes a radiation detector used to detect radiation such as X-rays and γ-rays.

The radiation detector includes a scintillator configured to emit light (scintillation light) in accordance with radiation that enters, and an optical sensor array including a plurality of optical sensors each configured to output an electric signal in accordance with the scintillation light. The scintillator is configured as a scintillator array in which blocks corresponding to scintillator pixels are formed in a matrix through division into pieces. The scintillator array is disposed on (aligned to) the optical sensor array, and is coupled to the optical sensors configured to detect light generated in the scintillator pixels.

DETAILED DESCRIPTION

One of the issues that the embodiments disclosed in the present specification and the accompanying drawings try to solve is to improve a reduction in yield due to misalignment in a scintillator array. However, the issues that the embodiments disclosed in the present specification and the accompanying drawings try to solve are not limited to the issue described above. It is possible to place, as other issues, issues corresponding to effects through configurations illustrated in the embodiments described later.

A radiation detector according to an embodiment includes a scintillator array, a sensor array, electronic circuitry, switches, and control circuitry. The scintillator array includes a plurality of scintillator pixels each configured to convert radiation into light. The sensor array includes a plurality of detection elements each configured to detect the light. The electronic circuitry is configured to output digital data on the basis of signals output from the detection elements. The switches are provided between the sensor array and the electronic circuitry. The control circuitry is configured to control the switches on the basis of a positional relation between the sensor array and the scintillator array.

The radiation detector according to the embodiment will now be described herein with reference to the accompanying drawings. Note that embodiments are not limited to the embodiments described below. Furthermore, it is possible to apply in principle the contents described in one embodiment to other embodiments.

Note that, although the X-ray detector will be described below as an example in the embodiment, the embodiment is not limited to the example. For example, the embodiment described below are also applicable to radiation detectors that detect gamma rays and other rays.

Furthermore, although the below embodiment describe, as an example, an X-ray CT device in which photon counting CT is executable, the embodiment is not limited to the example. For example, the embodiment described below are also applicable to radiation diagnostic devices including X-ray CT devices including integral-type (electric current mode measurement-type) detectors and radiation detectors configured to detect gamma rays and other rays.

Embodiment

Figure 1:
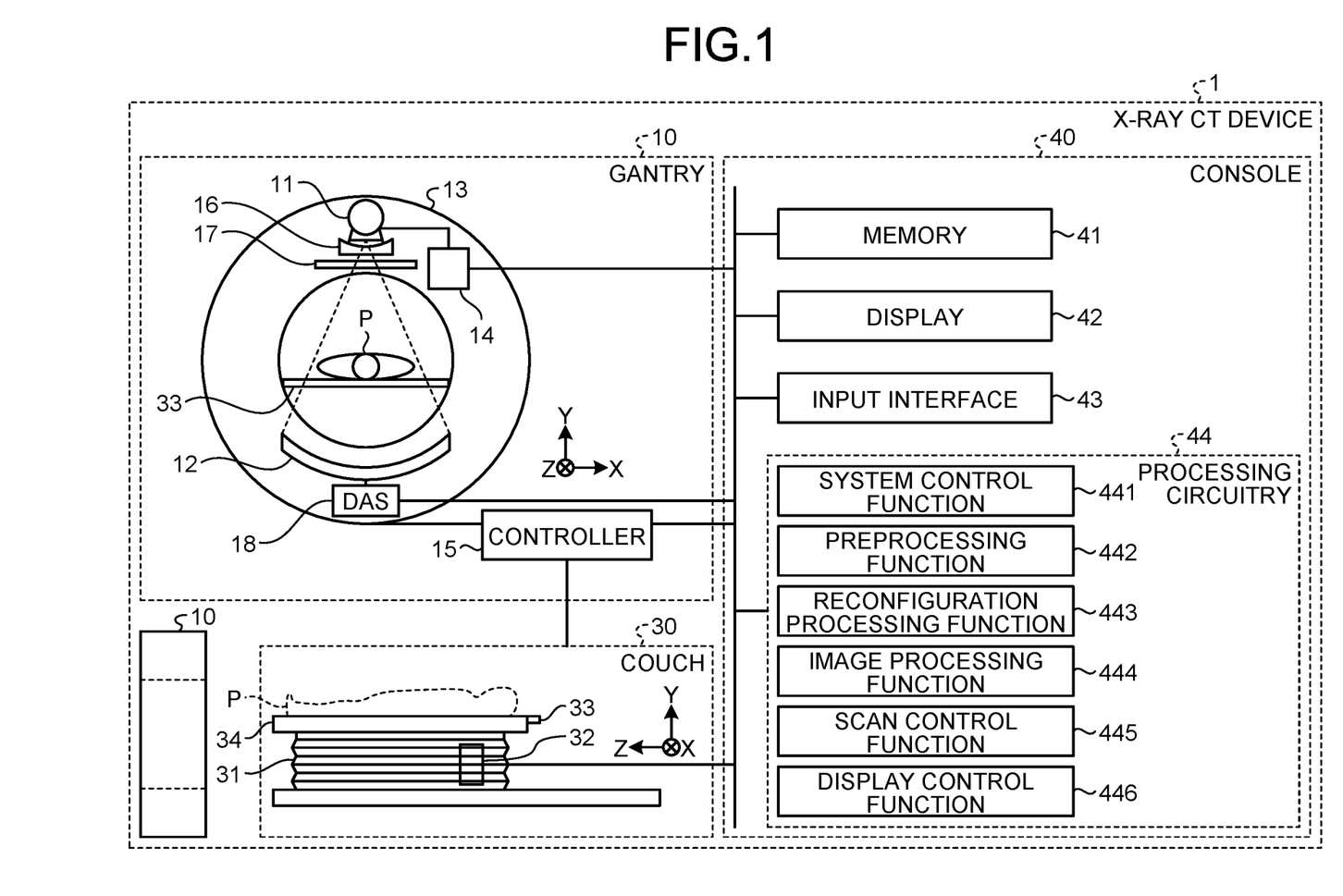
FIG. 1 is a view illustrating an example of a configuration of an X-ray CT device according to an embodiment.
Figure 2:
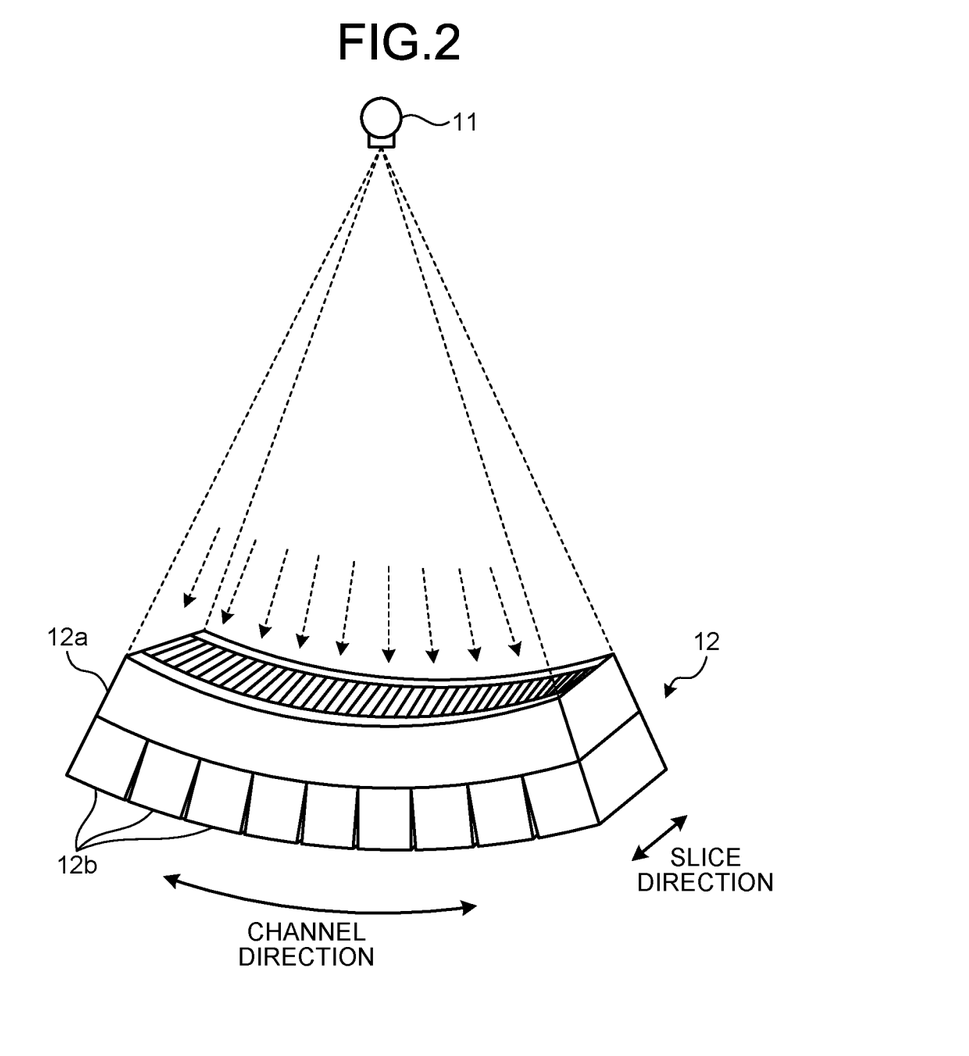
FIG. 2 is a view illustrating a configuration example of an X-ray detector according to the embodiment.

FIG. 1 is a view illustrating an example of a configuration of an X-ray CT device 1 according to the embodiment. As illustrated in FIG. 2, the X-ray CT device 1 according to the embodiment includes a gantry 10, a couch 30, and a console 40.

Note herein that, in FIG. 1, directions extending along a rotation axis of a rotation frame 13 or longer directions of a couchtop 33 of the couch 30, in a non-tilted state, are referred to as Z-axis directions. Furthermore, axis directions that are orthogonal to the Z-axis directions and that are horizontal to a floor face are referred to as X-axis directions. Furthermore, axis directions that are orthogonal to the Z-axis directions and that are vertical to the floor face are referred to as Y-axis directions. Note that, although the gantry 10 is illustrated at two locations in FIG. 1 because the gantry 10 is depicted in a plurality of directions for purpose of description, the gantry 10 included in the X-ray CT device 1 is only one.

The gantry 10 includes an X-ray tube 11, an X-ray detector 12, the rotation frame 13, an X-ray high-voltage device 14, a controller 15, a wedge 16, an X-ray limiter 17, and data acquisition systems (DASs) 18.

The X-ray tube 11 is a vacuum tube including a negative electrode (a filament) from which thermal electrons are generated, and a positive electrode (a target) with which the thermal electrons collide to generate X-rays. When the X-ray high-voltage device 14 applies a high voltage, the X-ray tube 11 allows thermal electrons to exit from the negative electrode and to reach the positive electrode to generate X-rays with which a subject P is irradiated. An example of the X-ray tube 11 is a rotating anode-type X-ray tube configured to allow thermal electrons to exit and reach the positive electrode that is rotating to generate X-rays.

The rotation frame 13 is an annular frame supporting the X-ray tube 11 and the X-ray detector 12 facing each other. The rotation frame 13 allows the controller 15 to rotate the X-ray tube 11 and the X-ray detector 12. For example, the rotation frame 13 is a cast product made of aluminum. Note that the rotation frame 13 is able to support the X-ray high-voltage device 14, the wedge 16, the X-ray limiter 17, and the DASs 18, for example, in addition to the X-ray tube 11 and the X-ray detector 12. Furthermore, the rotation frame 13 is able to support various components that are not illustrated in FIG. 1.

The wedge 16 is a filter configured to adjust an amount of X-rays that the X-ray tube 11 emits. Specifically, the wedge 16 is a filter configured to attenuate X-rays that have emitted from the X-ray tube 11 and pass therethrough such that the X-rays emitted from the X-ray tube 11 to the subject P is distributed in a predefined manner. For example, the wedge 16 is a filter such as a wedge filter or a bow-tie filter that is made of a material such as aluminum and that is processed to have a predetermined target angle and a predetermined thickness.

The X-ray limiter 17 includes a plurality of lead plates, for example, used to limit a range to be irradiated with X-rays passing through the wedge 16. The lead plates, for example, are combined to form slits. Note that the X-ray limiter 17 is sometimes referred to as a pre-subject collimator. Furthermore, although FIG. 1 illustrates a case where the wedge 16 is disposed between the X-ray tube 11 and the X-ray limiter 17, the X-ray limiter 17 may be disposed between the X-ray tube 11 and the wedge 16. In this case, the wedge 16 allows X-rays, which have emitted from the X-ray tube 11, and for which the range to be irradiated with the X-rays is limited by the X-ray limiter 17, to pass through, attenuating the X-rays.

The X-ray high-voltage device 14 includes electric circuitry including a transformer and a rectifier, for example, and further includes a high-voltage generator configured to generate a high voltage to be applied to the X-ray tube 11 and an X-ray controller configured to control an output voltage in accordance with X-rays that the X-ray tube 11 emits. For the high-voltage generator, a transformer style or an inverter style may be adopted. Note that the X-ray high-voltage device 14 may be provided to the rotation frame 13 or may be provided to a non-illustrated fixed frame.

The controller 15 includes processing circuitry including a central processing unit (CPU), for example, and a drive mechanism including a motor and an actuator, for example. The controller 15 is configured to accept an input signal from an input interface 43 to perform operation control for the gantry 10 and the couch 30. For example, the controller 15 is configured to perform control of allowing the rotation frame 13 to rotate, of allowing the gantry 10 to tilt, and of allowing the couch 30 and the couchtop 33 to operate. In an example case, the controller 15 is configured to cause, as control of causing the gantry 10 to tilt, the rotation frame 13 to rotate about an axis parallel to the X-axis direction on the basis of inclination angle (tilt angle) information that has been input. Note that the controller 15 may be provided to the gantry 10, or may be provided to the console 40.

The X-ray detector 12 is configured to output, each time an X-ray photon enters, a signal allowing an energy value of the X-ray photon to be measured. An X-ray photon is, for example, an X-ray photon that has emitted from the X-ray tube 11 and passed through the subject P. The X-ray detector 12 includes a plurality of detection elements each configured to output, each time an X-ray photon enters, a one-pulse electric signal (an analog signal). Counting electric signals (pulses) makes it possible to count X-ray photons that have entered each of the detection elements.

Furthermore, performing predetermined arithmetic processing on each of the signals makes it possible to measure an energy value of an X-ray photon that has caused the signal to be output. Note that, to reduce scattered X-rays, a collimator is provided on an X-ray incidence plane side of the X-ray detector 12. The collimator is sometimes referred to as a scattered ray removal grid or a post-subject collimator.

The detection elements described above are sensors each including a plurality of electrodes and each configured to detect radiation. For example, in each of the detection elements, a scintillator that generates light (scintillation light) in accordance with an X-ray photon that has entered and a complementary metal-oxide-semiconductor (CMOS) image sensor that converts the scintillation light into an electric signal are combined with each other. That is, the X-ray detector 12 is an indirect conversion-type detector in which fluorescent bodies that are to be excited through radiation to emit light and a light detector configured to convert the light that the fluorescent bodies have emitted into electric signals are combined with each other. Note that the configuration of the light detector will be described later.

The X-ray detector 12 includes the detection elements described above and a plurality of application specific integrated circuits (ASICs) that are respectively coupled to the detection elements and that are each configured to count X-ray photons that each of the detection elements has detected. The ASICs are each configured to discriminate, per wave height, electric pulses each having a height proportional to each of the charge amounts that the detection elements have output to count X-ray photons that have entered each of the detection elements. Furthermore, the ASICs are each configured to perform arithmetic processing on the basis of the magnitude of each charge to measure the energy of each of the X-ray photons being counted. Furthermore, the ASICs are each configured to output, as digital data, a result of counting of the X-ray photons to each of the DASs 18.

The DASs 18 are electronic circuitry configured to output digital data on the basis of signals output from the detection elements. For example, the DASs 18 are each configured to generate detection data (digital data) on the basis of a result of count processing, which is input from the X-ray detector 12. The detection data is, for example, a sinogram. The sinogram is data in which results of count processing for X-ray photons that have entered the detection elements at positions on the X-ray tube 11 are arranged. The sinogram is data in which results of count processing are arranged in a two-dimensional, orthogonal coordinate system having axes respectively extending in view directions and channel directions. For example, the DASs 18 are each configured to generate a sinogram per column extending in slice directions in the X-ray detector 12. Note herein that a result of count processing is data in which X-ray photons per energy bin are allocated. For example, the DASs 18 are each configured to count photons (X-ray photons) derived from X-rays that have emitted from the X-ray tube 11 and passed through the subject P to discriminate the energy of each of the X-ray photons being counted, and to regard the energy as a result of count processing. The DASs 18 are each configured to transfer the generated detection data to the console 40. The DASs 18 are each achieved by a processor, for example.

The data that the DASs 18 have each generated is sent, through optical communications, from a transmitter including a light emitting diode (LED), which is provided to the rotation frame 13, to a receiver including a photodiode, which is provided to a non-rotating portion (e.g., the fixed frame, which is omitted from the illustration in FIG. 1) of the gantry 10, and is then transferred to the console 40. Note herein that the non-rotating portion is, for example, the fixed frame that rotatably supports the rotation frame 13. Note that the method of sending data from the rotation frame 13 to the non-rotating portion of the gantry 10 is not limited to the optical communications, but any non-contact-type data transfer method or any contact-type data transfer method may be employed.

The couch 30 is a device that is configured to move and place a subject of imaging, i.e., the subject P, and that includes a base 31, a couch driver 32, the couchtop 33, and a support frame 34. The base 31 is a housing that supports the support frame 34 movably in a perpendicular direction. The couch driver 32 is a drive mechanism that is configured to move the couchtop 33 on which the subject P is placed in the longer axis direction of the couchtop 33, and that includes a motor and an actuator, for example. The couchtop 33 provided on a top surface of the support frame 34 is a plate on which the subject P is placed. Note that, in addition to the couchtop 33, the couch driver 32 may move the support frame 34 in the longer axis direction of the couchtop 33.

The console 40 includes a memory 41, a display 42, the input interface 43, and processing circuitry 44. Note that, although the console 40 is described as a separate body from the gantry 10, the gantry 10 may include the console 40 or some components of the console 40.

The memory 41 is achieved by, for example, a semiconductor memory element, such as a random-access memory (RAM) or a flash memory, a hard disk, or an optical disc. The memory 41 is configured to memorize, for example, projection data and CT image data. Furthermore, for example, the memory 41 is configured to memorize computer programs with which circuitry included in the X-ray CT device 1 achieves its functions. Note that the memory 41 may be achieved by a server group (cloud) coupled, via a network, to the X-ray CT device 1.

The display 42 is configured to display various types of information. For example, the display 42 is configured to display various types of images generated by the processing circuitry 44, and to display a graphical user interface (GUI) to accept various types of operations from an operator. For example, the display 42 is a liquid crystal display or a cathode ray tube (CRT) display. The display 42 may be a desktop type or a tablet terminal configured to be able to communicate in a wireless manner with the console 40 main body, for example.

The input interface 43 is configured to accept various types of input operations from the operator, to convert the accepted input operations into electric signals, and to output the converted electric signals to the processing circuitry 44. Furthermore, for example, the input interface 43 is configured to accept, from the operator, input operations such as reconfiguration conditions for reconfiguring CT image data and image processing conditions for generating post-processed images from CT image data.

For example, the input interface 43 is achieved by a mouse, a keyboard, a trackball, switches, buttons, a joystick, a touchpad having an operation face to be touched for an input operation, a touchscreen in which a display screen and a touchpad are integrated with each other, non-contact input circuitry using an optical sensor, and voice input circuitry. Note that the input interface 43 may be provided to the gantry 10. Furthermore, the input interface 43 may be a tablet terminal configured to be able to communicate in a wireless manner with the console 40 main body, for example. Furthermore, the input interface 43 is not limited to those that include physical operation parts such as a mouse and a keyboard. For example, examples of the input interface 43 include processing circuitry for electric signals. The processing circuitry is configured to receive an electric signal corresponding to an input operation, from an external input device provided separately from the console 40, and to output the electric signal to the processing circuitry 44.

The processing circuitry 44 is configured to wholly control how the X-ray CT device 1 operates. For example, the processing circuitry 44 is configured to execute a system control function 441, a preprocessing function 442, a reconfiguration processing function 443, an image processing function 444, a scan control function 445, and a display control function 446. Note herein that, for example, the processing functions to be executed by the components of the processing circuitry 44 illustrated in FIG. 1, which are the system control function 441, the preprocessing function 442, the reconfiguration processing function 443, the image processing function 444, the scan control function 445, and the display control function 446, each take the form of a computer program executable by a computer. The computer programs are recorded in the memory 41. The processing circuitry 44 is, for example, a processor configured to read and execute the computer programs from the memory 41 to achieve the functions corresponding to the read computer programs. In other words, the processing circuitry 44 that has read the computer programs possesses the functions illustrated in the processing circuitry 44 in FIG. 1.

Note that, although FIG. 1 has illustrated the case where the processing circuitry 44 is configured to solely achieve the processing functions of the system control function 441, the preprocessing function 442, the reconfiguration processing function 443, the image processing function 444, the scan control function 445, and the display control function 446, the embodiment is not limited to the case. For example, the processing circuitry 44 may include a plurality of independent processors in a combined manner. The processors may respectively execute computer programs to achieve the processing functions. The processing functions that the processing circuitry 44 possesses may be achieved appropriately in an integrated manner into single processing circuitry or in a dispersed manner among a plurality of portions of processing circuitry.

The system control function 441 is configured to control various types of functions of the processing circuitry 44 on the basis of input operations accepted from the operator via the input interface 43.

The preprocessing function 442 is configured to perform preprocessing such as logarithmic conversion processing, offset correction processing, inter-channel sensitivity correction processing, and beam hardening corrections on detection data output from the DASs 18 to generate projection data.

The reconfiguration processing function 443 is configured to perform reconfiguration processing using a filter correction back projection method and a successive approximation reconfiguration method, for example, on the projection data generated by the preprocessing function 442 to generate CT image data. The reconfiguration processing function 443 is configured to store the reconfigured CT image data in the memory 41.

Note herein that projection data to be generated from a result of counting, which is to be acquired through photon counting CT, includes information on the energy of X-rays, which is attenuated as the X-rays pass through the subject P. Therefore, for example, the reconfiguration processing function 443 is able to reconfigure CT image data of a certain energy component. Furthermore, for example, the reconfiguration processing function 443 is able to reconfigure CT image data of each of a plurality of energy components.

Furthermore, for example, the reconfiguration processing function 443 is able to allocate a color tone in accordance with an energy component to each pixel of CT image data for each energy component to generate image data superimposed with a plurality of pieces of CT image data colored in accordance with the energy components. Furthermore, for example, the reconfiguration processing function 443 is able to utilize a K absorption edge inherent to a substance to generate image data allowing the substance to be identified. Other image data that the reconfiguration processing function 443 generates include, for example, monochromatic X-ray image data, density image data, and effective atomic number image data.

To reconfigure CT image data, projection data covering the full circumference, that is, 360 degrees, of the subject or projection data covering 180 degrees+a fan angle, in the case of a half scan method, is required. Any reconfiguration methods are applicable to the present embodiment. For ease of description, a reconfiguration (full scan reconfiguration) method that uses projection data covering the full circumference, that is, 360 degrees, of the subject for reconfiguration is used in the below description.

The image processing function 444 is configured to convert, using a known method, the CT image data generated by the reconfiguration processing function 443 on the basis of an input operation accepted from the operator via the input interface 43, into image data such as a tomographic view of a desired cross section and a three-dimensional image created through rendering processing. The image processing function 444 is configured to store the converted image data in the memory 41.

The scan control function 445 is configured to control CT scanning to be carried out on the gantry 10. For example, the scan control function 445 is configured to control the operation of the X-ray high-voltage device 14, the X-ray detector 12, the controller 15, the DASs 18, and the couch driver 32 to control collection processing of results of counting carried out on the gantry 10. In an example case, the scan control function 445 is configured to control collection processing of projection data during imaging for collecting a positioning image (a scanogram image) and actual imaging (scanning) for collecting images used for diagnoses.

The display control function 446 is configured to control the display 42 to display various types of image data that the memory 41 stores therein.

Note herein that, for example, the system control function 441, the preprocessing function 442, the reconfiguration processing function 443, the image processing function 444, the scan control function 445, and the display control function 446 that the processing circuitry 44 possesses are recorded in the memory 41 each in the form of a computer program executable by the computer. The processing circuitry 44 is a processor configured to read and execute the computer programs from the memory 41 to achieve the functions corresponding to the computer programs. In other words, the processing circuitry 44 having read the computer programs corresponding to the functions possesses the system control function 441, the preprocessing function 442, the reconfiguration processing function 443, the image processing function 444, the scan control function 445, and the display control function 446 illustrated in the processing circuitry 44 in FIG. 1.

Note that, although FIG. 1 has illustrated the case where the processing circuitry 44 is configured to solely achieve the processing functions of the system control function 441, the preprocessing function 442, the reconfiguration processing function 443, the image processing function 444, the scan control function 445, and the display control function 446, the embodiment is not limited to the case. For example, the processing circuitry 44 may include a plurality of independent processors in a combined manner. The processors may respectively execute computer programs to achieve the processing functions. The processing functions that the processing circuitry 44 possesses may be achieved appropriately in an integrated manner into single processing circuitry or in a dispersed manner among a plurality of portions of processing circuitry.

Note that the term "processor" used and described above means, for example, circuitry including a central processing unit (CPU), a graphics processing unit (GPU), an application specific integrated circuit (ASIC), and a programmable logic device (e.g., a simple programmable logic device (SPLD), a complex programmable logic device (CPLD), and a field programmable gate array (FPGA)). The processor reads the computer programs stored in memory circuitry and executes the read computer programs to achieve the functions. Note that, instead of storing computer programs in memory circuitry, such a configuration may be applied that computer programs are directly incorporated in circuitry in a processor. In this case, the processor reads the computer programs incorporated in the circuitry and executes the read computer programs to achieve the functions. The processors according to the present embodiment are not limited to those where each of the processors is configured as single circuitry. However, a plurality of pieces of independent circuitry may be combined to configure a single processor to achieve the functions.

By the way, when a scintillator array is to be mounted on an optical sensor array, mechanical positional displacement in alignment (misalignment) may occur. When the amount of the positional displacement falls within a certain range, the positional displacement is regarded as acceptable. However, if the amount of positional displacement falls outside of the allowable range in a detector, the detector is regarded as an unacceptable product. It is not possible to mount such an unacceptable product on an X-ray CT device. Therefore, the yield of X-ray detectors lowers. When the yield lowers, such X-ray detectors and X-ray CT devices may lead to an increase in cost. Furthermore, since the higher the definition of pixels, the severer the alignment accuracy, such a correction method is required that achieves the accuracy at a level of several micrometers (μm).

Then, the X-ray CT device 1 according to the embodiment includes a configuration described below in order to improve a reduction in yield due to misalignment in a scintillator array.

A configuration example of the X-ray detector 12 according to the embodiment will now be described with reference to FIG. 2. FIG. 2 is a view illustrating the configuration example of the X-ray detector 12 according to the embodiment. For example, as illustrated in FIG. 2, the X-ray detector 12 includes a collimator unit 12a and a plurality of detector modules 12b. Note that, in FIG. 2, dotted arrows illustrate an irradiation direction of X-rays. Furthermore, in the below description, a circumferential direction around the X-ray tube 11 will be referred to as the channel direction, while a direction along the Z axis serving as the rotation axis of the rotation frame 13 described above will be referred to as the slice direction. Furthermore, to describe positions on the X-ray detector 12 when the X-ray detector 12 is mounted on the X-ray CT device 1, positions nearer to the X-ray tube 11 are described as "upper (or above, upper part, or top surface, for example)", while positions farther from the X-ray tube 11 are described as "lower (or below, lower part, or lower surface, for example)".

The collimator unit 12a is configured to remove scattered rays from X-rays entering the detector modules 12b. Specifically, the collimator unit 12a is formed into a substantially arc shape about the X-ray tube 11, and is disposed on a front side of the detector modules 12b in the irradiation direction of X-rays. For example, the collimator unit 12a is formed by attaching in the irradiation direction of X-rays a plurality of collimator plates to a support member formed into an arc shape in the channel direction.

The detector modules 12b are arranged and disposed on an outer circumference side of the collimator unit 12a in the channel direction. Note that, although FIG. 2 has illustrated the case where the detector modules 12b are one-dimensionally disposed in the channel directions, the embodiment is not limited to the case. For example, the detector modules 12b may be two-dimensionally disposed in the channel direction and the slice direction.

Figure 3:
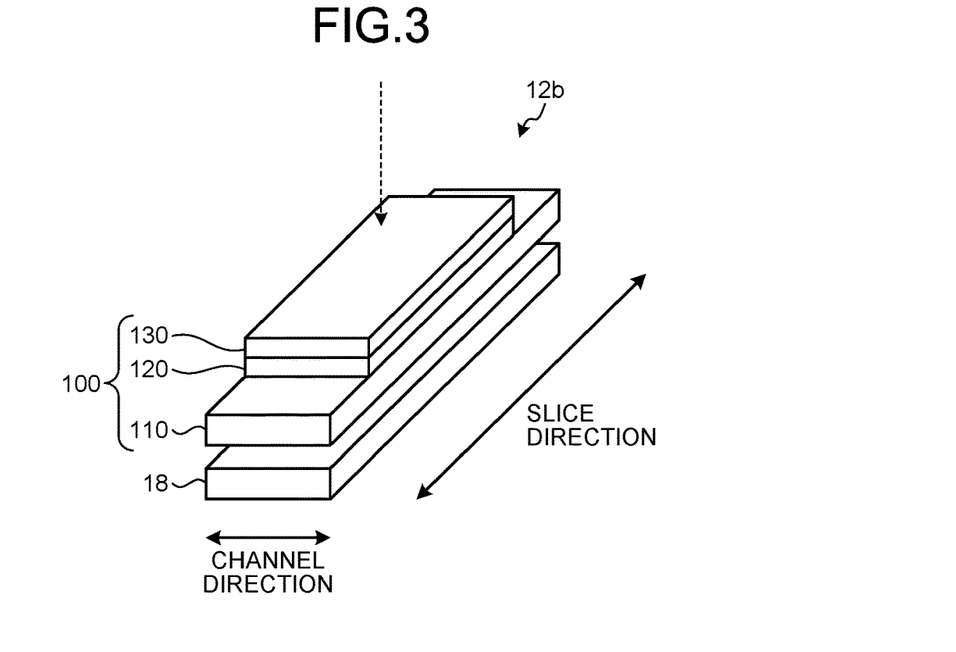
FIG. 3 is a view illustrating a configuration example of a detector module according to the embodiment.

A configuration example of one of the detector modules 12b according to the embodiment will now be described with reference to FIG. 3. FIG. 3 is a view illustrating the configuration example of one of the detector modules 12b according to the embodiment. Note that, in FIG. 3, a dotted arrow illustrates the irradiation direction of X-rays.

As illustrated in FIG. 3, for example, the detector module 12b includes one of the DASs 18 and a detector pack 100. The detector pack 100 includes a plate 110, an avalanche photodiode (APD) array 120, and a scintillator array 130.

The DAS 18 is configured to perform amplification processing and analog-to-digital (A/D) conversion processing, for example, on data of the intensity distribution of X-rays to be detected by the detector pack 100, to generate raw data, and to output the generated raw data. The DAS 18 is supported, by a non-illustrated support member, inside of the detector module 12b. Furthermore, an X-ray shielding plate may be provided between the DAS 18 and the detector pack 100 in order to prevent X-rays that directly enter from affecting the processing.

The plate 110 is a member configured to support the APD array 120 and the scintillator array 130. The APD array 120 and the scintillator array 130 adhere to each other with a transparent adhesive (e.g., an adhesion sheet). Note that the adhesive may be any type, as long as it becomes hardened with ultraviolet (UV) rays or heat, for example.

The APD array 120 is, for example, a complementary metal-oxide semiconductor (CMOS) image sensor formed from a silicon (Si) wafer. The APD array 120 is configured to convert light (scintillation light) to be generated by the scintillator array 130 into an electric signal in accordance with the energy of the scintillation light.

The scintillator array 130 is formed of a scintillator crystal material that emits light as X-rays enter. For example, the scintillator array 130 is configured to emit light (scintillation light) at an amount of light in accordance with the energy of X-rays entered via the collimator unit 12a. Examples of the scintillator crystal material include GSO ($Gd_2SiO_5$:Ce), BGO ($Bi_4Ge_3O_{12}$), LSO ($Lu_2SiO_5$:Ce), and garnet-based materials such as lutetium aluminum garnet (LuAG) and yttrium gallium garnet (YGG).

As described above, the detector module 12b is formed by making the DAS 18 and the detector pack 100 into a module. Therefore, for example, even if a failure occurs in one of the detector packs 100, it is possible to replace, per module, the detector pack 100 in which the failure has occurred.

Note that, although the case has been described, as an example, where the DAS 18 and the detector pack 100 are made into a module, the embodiment is not limited to the case. For example, the collimator unit 12a may be divided per the detector pack 100 to make, into a module, the detector pack 100, the DAS 18, and the collimator unit 12a. Even in such a case, it is still possible to replace, per module, the detector pack 100 in which a failure has occurred.

Furthermore, although the embodiment has described the case where the DASs 18 are provided in the X-ray detector 12, the embodiment is not limited to the case. For example, the DASs 18 may be provided outside of the X-ray detector 12. In this case, it is possible to provide the DASs 18 to the gantry 10 or a console 40.

Note that, although FIG. 3 has described the configuration of the detector module 12b, the detector modules 12b mounted on the X-ray detector 12 each have a similar or identical configuration. That is, in the X-ray detector 12, the detector packs 100 are arrayed in predetermined directions (e.g., the channel direction).

Figure 4:
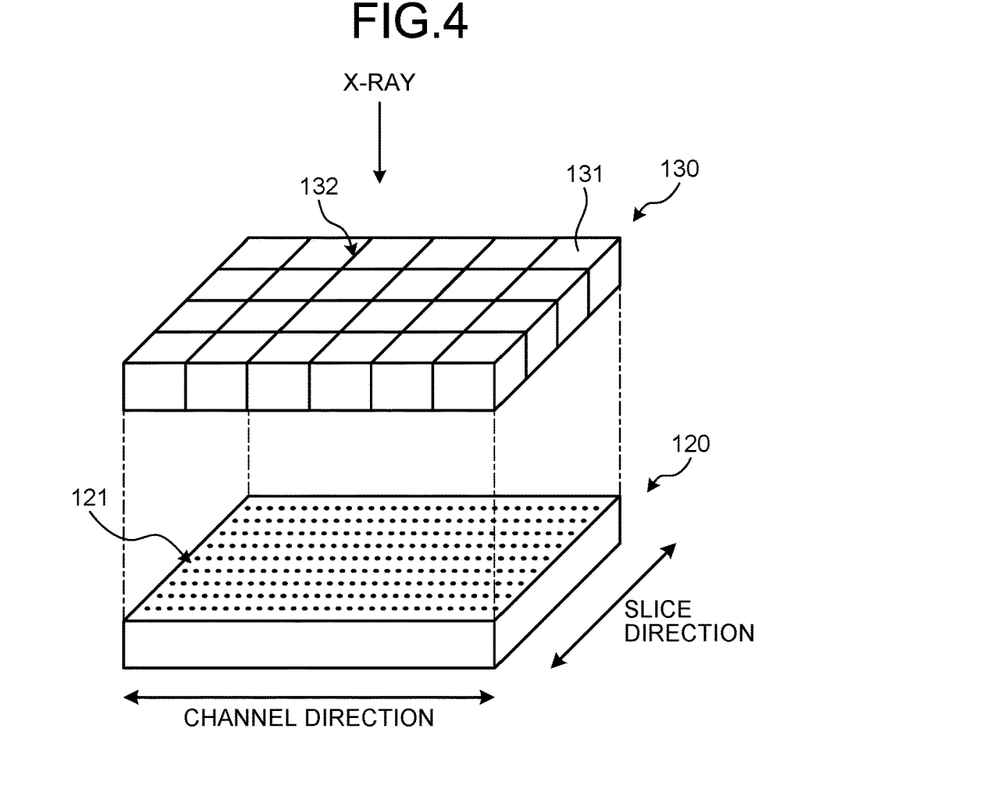
FIG. 4 is a view illustrating a configuration example of an avalanche photodiode (APD) array according to the embodiment.

A configuration example of the APD array 120 according to the embodiment will now be described with reference to FIG. 4. FIG. 4 is a view illustrating the configuration example of the APD array 120 according to the embodiment. Note that, in FIG. 4, a solid arrow illustrates the irradiation direction of X-rays.

As illustrated in FIG. 4, the APD array 120 includes a plurality of single photon avalanche diodes (SPADs) 121 each configured to detect light. The SPADs 121 are arrayed, for example, into a grid on a top surface (a surface being in contact with the scintillator array 130) of the APD array 120. Each of the SPADs 121 is formed smaller than each of a plurality of scintillator pixels 131. Note that the APD array 120 is an example of a "sensor array". Furthermore, each of the SPADs 121 is an example of a "detection element".

The scintillator array 130 includes the scintillator pixels 131 each configured to convert radiation into light. For example, the scintillator crystal material is divided by a partition wall layer 132 having a grid shape to form the scintillator pixels 131. The partition wall layer 132 is formed with a desired method such as a method of filling a reflective resin in grooves formed on a scintillator crystal material or a method of using stealth laser to form a modifying layer inside of a scintillator crystal material. The scintillator array 130 formed with the scintillator pixels 131 is laminated on the APD array 120.

Note that the contents illustrated in FIG. 4 are mere examples, and the embodiment is not limited to the illustrated contents. For example, although FIG. 4 has described the case where the SPADs 121 are arrayed into a grid (in the channel direction and the slice direction), the embodiment is not limited to the case. For example, the SPADs 121 may be arrayed in a desired arraying shape such as a honeycomb shape (a shape where regular hexagons are laid). However, it is preferable that the SPADs 121 be uniformly arrayed in a non-sparse manner.

Furthermore, although FIG. 4 has illustrated the case where the scintillator pixels 131 are arrayed six in the channel direction by four in the slice direction, the embodiment is not limited to the case. It is possible to array the desired number of the scintillator pixels 131 in accordance with the configuration of the X-ray detector 12.

Note herein that, even if the scintillator array 130 is not correctly aligned and positional displacement has occurred when the scintillator array 130 is laminated on the APD array 120, the X-ray detector 12 makes it possible to secure active areas each having a dimension similar or identical to a dimension of each of the active areas when the scintillator array 130 has been correctly aligned.

Figure 5:
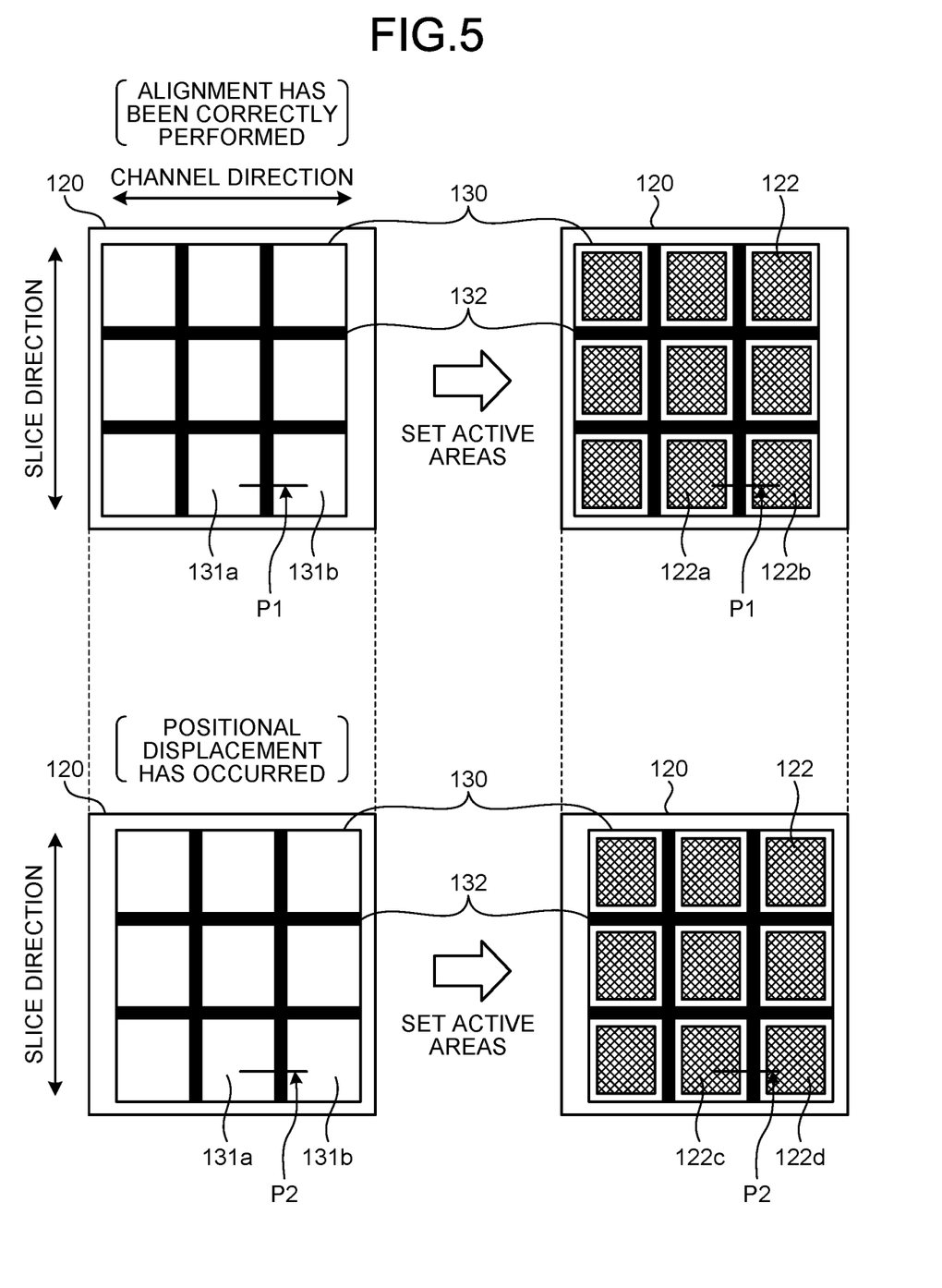
FIG. 5 is a view for describing how to set active areas according to the embodiment.
Figure 6:
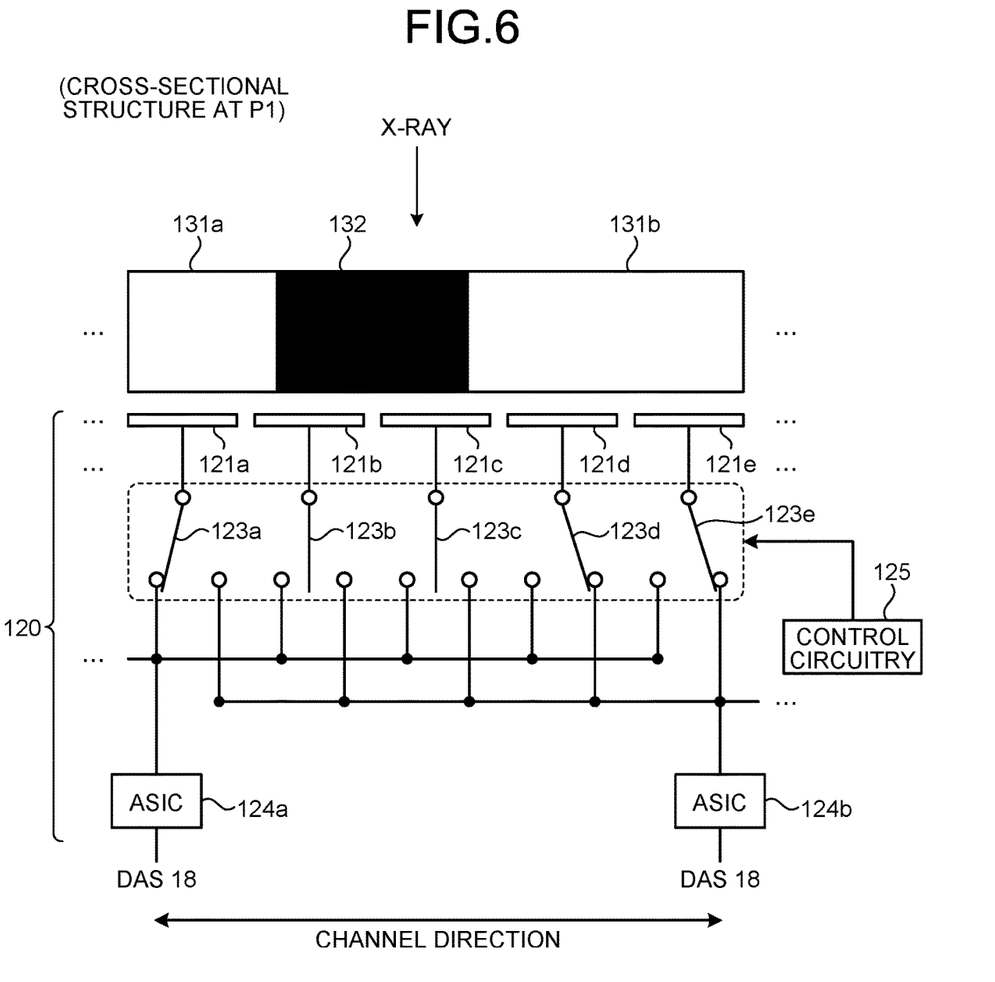
FIG. 6 is a view for describing how to set the active areas according to the embodiment.
Figure 7:
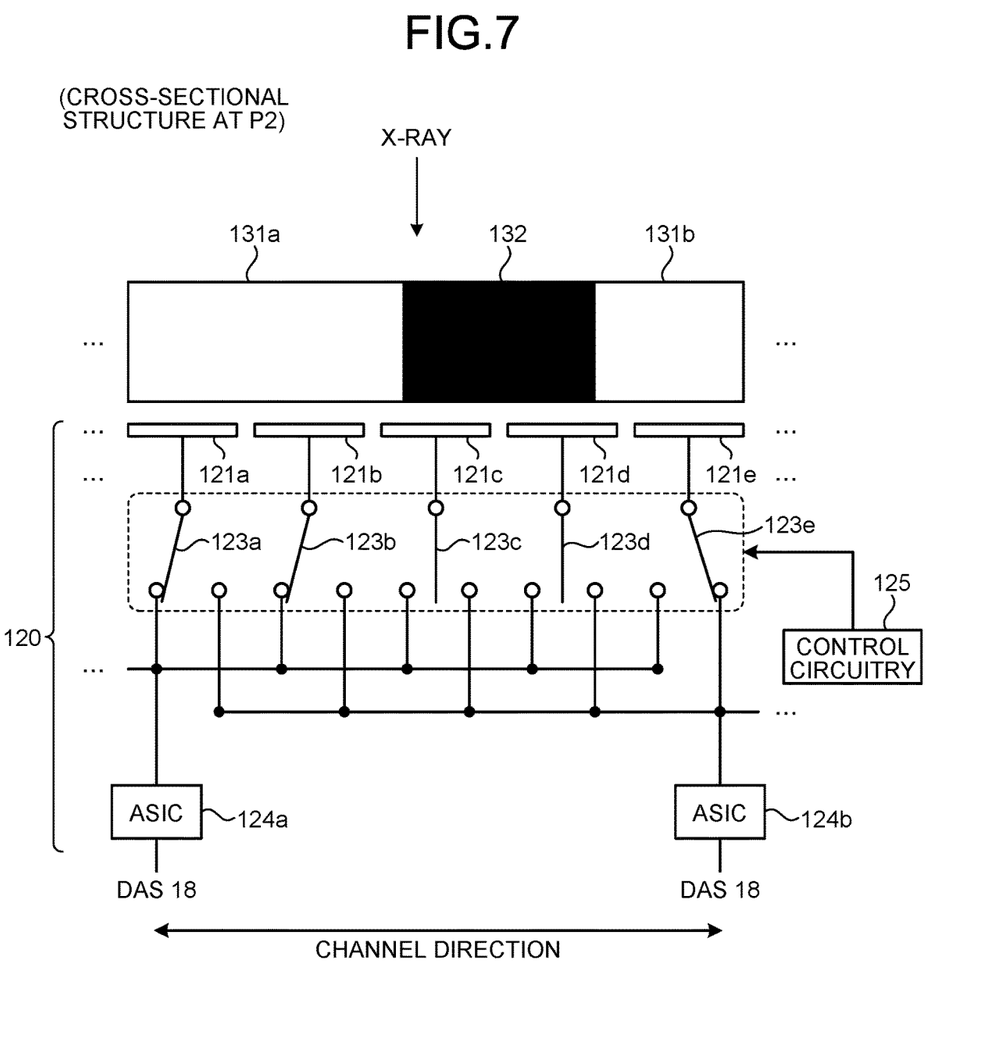
FIG. 7 is a view for describing how to set the active areas according to the embodiment.

How to set the active areas according to the embodiment will now be described with reference to FIGS. 5, 6, and 7. FIGS. 5, 6, and 7 are views for describing how to set the active areas according to the embodiment. FIG. 5 illustrates an example of the APD array 120 and the scintillator array 130 when viewed from above (in the irradiation direction of X-rays). Furthermore, FIG. 6 illustrates a cross-sectional structure at a position P1 in FIG. 5. Furthermore, FIG. 7 illustrates a cross-sectional structure at a position P2 in FIG. 5. Note that the position P1 and the position P2 correspond to the identical position on the APD array 120.

Note that an upper side of FIG. 5 illustrates a case when alignment has been correctly performed, while a lower side of FIG. 5 illustrates a case when positional displacement has occurred. Specifically, in the upper side and the lower side of FIG. 5, the positions of the APD arrays 120 correspond to each other. However, in the lower side of FIG. 5, the position of the scintillator array 130 is displaced rightward in the figure, compared with the upper side of FIG. 5.

As illustrated in the upper side of FIG. 5, when the scintillator array 130 is correctly aligned on the APD array 120, active areas 122 are set (defined) in ranges, which respectively correspond to the scintillator pixels 131, on the top surface of the APD array 120. Specifically, an active area 122a is set in a range corresponding to a scintillator pixel 131a, while an active area 122b is set in a range corresponding to a scintillator pixel 131b. Note that, when the scintillator pixels 131a and 131b are not differentiated from each other, they are collectively described as the "scintillator pixels 131". Furthermore, when the active areas 122a and 122b are not differentiated from each other, they are collectively described as the "active areas 122".

On the other hand, as illustrated in the lower side of FIG. 5, when rightward positional displacement has occurred, the active areas 122 are set in ranges, which respectively correspond to the scintillator pixels 131, on the top surface of the APD array 120. Specifically, an active area 122c is set in a range corresponding to the scintillator pixel 131a, while an active area 122d is set in a range corresponding to the scintillator pixel 131b.

Note herein that, although the active area 122c is set at a position displaced rightward due to the positional displacement, compared with the active area 122a, it is still possible to secure a dimension similar or identical to the dimension of the active area 122a. Furthermore, although the active area 122d is set at a position displaced rightward due to the positional displacement, compared with the active area 122b, it is still possible to secure a dimension similar or identical to the dimension of the active area 122b. The reason is that the SPADs 121 specifying each of the active areas 122 are determined (selected) on the basis of a positional relation between the APD array 120 and the scintillator array 130. Next, how to determine the SPADs 121 on the basis of the positional relation between the APD array 120 and the scintillator array 130 will now be described with reference to FIGS. 6 and 7.

In the examples illustrated in FIGS. 6 and 7, the APD array 120 includes SPADs 121a, 121b, 121c, 121d, and 121e, switches 123a, 123b, 123c, 123d, and 123e, ASICs 124a and 124b, and control circuitry 125. Note that, when the SPADs 121a, 121b, 121c, 121d, and 121e are not differentiated from each other, they are collectively described as the "SPADs 121". Furthermore, when the switches 123a, 123b, 123c, 123d, and 123e are not differentiated from each other, they are collectively described as the "switches 123". Furthermore, when the ASICs 124a and 124b are not differentiated from each other, they are collectively described as "ASICs 124".

The switches 123 are provided between the APD array 120 (the SPADs 121) and the DASs 18. For example, the switches 123 are provided, on a one-by-one basis, to the SPADs 121, and are each configured to be able to select a destination of a signal to be output from each of the SPADs 121 to one of the ASIC 124a, the ASIC 124b, and OFF (not send the signal to anywhere).

Each of the ASICs 124 is electronic circuitry configured to output digital data on the basis of a signal output from each of the SPADs 121. For example, the ASICs 124 are each configured to bundle signals output from the switches 123 to generate (measure) digital data in accordance with light received by each of the scintillator pixels 131.

Specifically, the ASIC 124a is configured to generate digital data in accordance with light received by the scintillator pixel 131a. Furthermore, the ASIC 124b is configured to generate digital data in accordance with light received by the scintillator pixel 131b. Then, the ASICs 124 are each configured to output results of counting of X-ray photons to each of the DASs 18 as digital data.

The control circuitry 125 includes processing circuitry including a CPU, for example, and is configured to control the switches 123 on the basis of the positional relation between the APD array 120 and the scintillator array 130. For example, the control circuitry 125 is configured to control the switches 123 to control a destination of a signal to be output from each of the SPADs 121 to one of the ASIC 124a, the ASIC 124b, and OFF. Note that the control circuitry 125 is an example of a "control part".

Note herein that, at the position P1, as illustrated in FIG. 6, the scintillator pixel 131a is disposed above the SPAD 121a, the partition wall layer 132 is disposed above the SPADs 121b and 121c, and the scintillator pixel 131b is disposed above the SPADs 121d and 121e. In this case, the control circuitry 125 sets a target to couple the switch 123a to the ASIC 124a, sets the switches 123b and 123c to OFF, and sets a target to couple the switches 123d and 123e to the ASIC 124b. Therefore, the control circuitry 125 causes the ASIC 124a to generate digital data in accordance with light received by the scintillator pixel 131a, while causing the ASIC 124b to generate digital data in accordance with light received by the scintillator pixel 131b.

On the other hand, at the position P2, as illustrated in FIG. 7, the scintillator pixel 131a is disposed above the SPADs 121a and 121b, the partition wall layer 132 is disposed above the SPADs 121c and 121d, and the scintillator pixel 131b is disposed above the SPAD 121e. In this case, the control circuitry 125 sets a target to couple the switches 123a and 123b to the ASIC 124a, sets the switches 123c and 123d to OFF, and sets a target to couple the switch 123e to the ASIC 124*b*. Therefore, the control circuitry 125 causes the ASIC 124*a* to generate digital data in accordance with light received by the scintillator pixel 131*a*, while causing the ASIC 124*b* to generate digital data in accordance with light received by the scintillator pixel 131*b*.

As described above, the control circuitry 125 determines a predetermined number of (a plurality of) SPADs 121, among the SPADs 121, specifying each of the active areas 122 on the basis of the positional relation between the APD array 120 and the scintillator array 130. That is, the control circuitry 125 is configured to control the switches 123 to allow the SPADs 121 included in a range corresponding to each of the scintillator pixels 131 to be substantially uniform in number. Therefore, even if positional displacement has occurred when the scintillator array 130 is laminated on the APD array 120, the control circuitry 125 makes it possible to secure active areas each having a dimension similar or identical to a dimension of each of active areas when the scintillator array 130 has been correctly aligned.

Note that X-rays entering the scintillator array 130 are converted into scintillation light for each of the scintillator pixels 131. Then, the scintillation light is converted into an electric signal by the SPADs 121 included, at a predetermined number, in a range corresponding to each of the scintillator pixels 131. That is, the SPADs 121 included, at a predetermined number, in a range corresponding to each of the scintillator pixels 131 function as an active area. Therefore, the scintillator pixel 131 and an active area associated with each other on a one-by-one basis correspond to one pixel (segment) in a medical image (CT image).

Furthermore, for example, it is possible to estimate the positional relation between the APD array 120 and the scintillator array 130 on the basis of the intensity, acquired when X-rays (radiation) are emitted, of an output signal (image) from each of the SPADs 121. For example, after the X-ray detector 12 has been assembled, when the X-ray detector 12 is to be inspected in the course of manufacturing the X-ray detector 12, the X-ray detector 12 is irradiated with X-rays to collect respective output signals from the SPADs 121. Then, the control circuitry 125 controls the switches 123 on the basis of the intensity of the output signals respectively acquired from the SPADs 121. For example, the control circuitry 125 refers to the intensity of the output signals respectively acquired from the SPADs 121 to estimate the positions of the scintillator pixels 131 and the partition wall layer 132 on the basis of the intensity of the output signals. Then, the control circuitry 125 performs switch control to bundle outputs of the SPADs 121 included, at a predetermined number, in a range corresponding to each of the scintillator pixels 131.

Note that the contents illustrated in FIGS. 5, 6, and 7 are mere examples, and the embodiment is not limited to the illustrated contents. For example, although FIGS. 5, 6, and 7 have illustrated the cases where positional displacement has occurred in the channel direction, the embodiment is not limited to the cases. For example, as to the positional displacement in not only the channel direction, but also the slice direction and both the channel direction and the slice direction, the control circuitry 125 is able to similarly set the active areas 122 on the basis of the positional relation between the APD array 120 and the scintillator array 130.

Furthermore, although, in the case illustrated in FIG. 5, the dimensions of the active areas 122 are respectively smaller each by a certain amount than the dimensions of the scintillator pixels 131, the embodiment is not limited to the case. For example, the dimensions of the active areas 122 may be respectively set similar or identical to the dimensions of the scintillator pixels 131. However, to reduce the leakage (cross talk) of scintillation light among the scintillator pixels 131, it is preferable that the dimensions of the active areas 122 be respectively smaller each by a certain amount than the dimensions of the scintillator pixels 131.

Furthermore, although FIGS. 6 and 7 have described the cases where the switches 123 are provided, on a one-by-one basis, to the SPADs 121, the embodiment is not limited to the cases. For example, the switches 123 may be each provided, on a one-by-one basis, to a group of SPADs, which includes a predetermined number of the SPADs 121 among the SPADs 121. The predetermined number represents an integer of 1 or greater. As an example, when the SPAD 121*a* and the SPAD 121*b* are specified as a group of SPADs, one of the switches 123 may be provided to the two SPADs 121*a* and 121*b*.

Furthermore, FIGS. 6 and 7 have described the cases where the two ASICs 124 are selectable as targets for coupling from the switches 123, the embodiment is not limited to the cases. The ASICs 124 to be selectable as targets for coupling from the switches 123 may be set at a desired number. Furthermore, the ASICs 124 to be selectable as targets for coupling may vary, in number, among the switches 123. For example, it is preferable that the nearer the positions at which the SPADs 121 are disposed to the partition wall layer 132 when alignment has been performed correctly, the more the number of the ASICs 124 to be set and selectable as targets for coupling, while it is preferable that the farther the positions at which the SPADs 121 are disposed from the partition wall layer 132, the less the number of the ASICs 124 to be set and selectable as targets for coupling.

As described above, the X-ray detector 12 according to the embodiment includes the scintillator arrays 130, the APD arrays 120, the DASs 18, the switches 123, and the control circuitry 125. The scintillator arrays 130 each include the scintillator pixels each configured to convert radiation into light. The APD arrays 120 each include the SPADs 121 each configured to detect the light. The DASs 18 are each configured to output digital data on the basis of a signal output from each of the SPADs 121. The switches 123 are provided between each of the APD arrays 120 and each of the DASs 18. The control circuitry 125 is configured to control the switches 123 on the basis of the positional relation between each of the APD arrays 120 and each of the scintillator arrays 130. With this configuration, the X-ray detector 12 according to the embodiment makes it possible to improve a reduction in yield due to misalignment of each of the scintillator arrays 130.

For example, even when positional displacement (an amount of displacement) has occurred on a product to an extent that the product was conventionally regarded as an unacceptable product, the X-ray detector 12 according to the embodiment determines a predetermined number (a plurality) of the SPADs 121, which specify each of the active areas 122, on the basis of the positional relation between each of the APD arrays 120 and each of the scintillator arrays 130. Therefore, the X-ray detector 12 makes it possible to not only prevent a reduction in dimension of each of the active areas, but also secure active areas each having a dimension similar or identical to a dimension of each of the active areas when alignment has been performed correctly. Therefore, even when positional displacement (an amount of displacement) has occurred on a product to an extent that the product was regarded as an unacceptable product, it is possible to mount the X-ray detector 12 on the X-ray CT device 1, making it possible to improve a reduction in yield, as well as to further improve a manufacturing cost.

Furthermore, the higher the definition of the X-ray detector 12, the severer the alignment accuracy. However, the X-ray detector 12 according to the embodiment having the configuration described above reduces the negative effects of misalignment, making it possible to reduce the negative effects of misalignment even when a high-definition X-ray detector 12 is used, as well as to improve a reduction in yield.

Note that, in the present embodiment, it is not limited to a case where, even when the term "substantially uniform" is used, the numbers of the SPADs 121 included in respective ranges corresponding to the scintillator pixels 131 always fully coincide with each other. It is intended that a case where such numbers vary (are not uniform) is included within a range where the effects according to the embodiment are not impaired.

Furthermore, although the above embodiment has described the case where the SPADs 121 are applied as CMOS image sensors, the embodiment is not limited to the case. For example, high-gain, charge conveying-type diodes may be applied as CMOS image sensors.

First Modification

For example, although the above embodiment has described the case where the comprehensive negative effects of positional displacement due to the misalignment of each of the scintillator arrays 130 are reduced, the embodiment is not limited to the case. For example, the X-ray detector 12 is also able to reduce the negative effects of local positional displacement that occurs due to a thinned partition wall layer.

That is, the control circuitry 125 is configured to adjust light-receiving positions (active areas) of each of the APD arrays 120, which correspond to some scintillator pixels 131 among the scintillator pixels 131, on the basis of positional displacement of some scintillator pixels 131 (lying locally) among the scintillator pixels 131.

Figure 8:
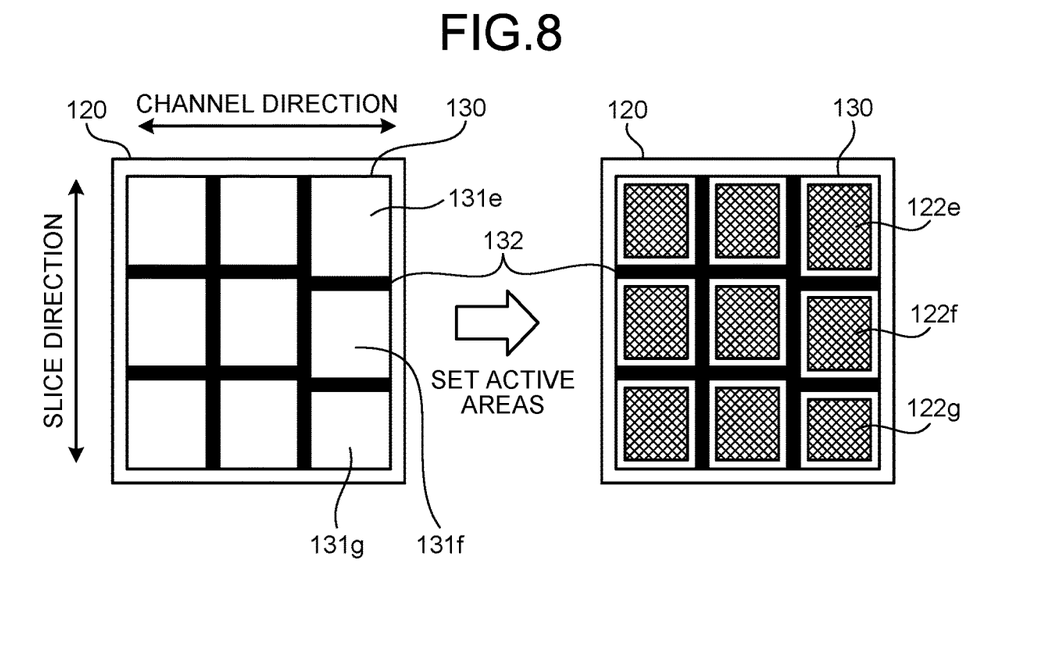
FIG. 8 is a view for describing how to set active areas according to a first modification of the embodiment.

How to set active areas according to a first modification of the embodiment will now be described with reference to FIG. 8. FIG. 8 is a view for describing how to set active areas according to the first modification of the embodiment. FIG. 8 illustrates an example of the APD array 120 and the scintillator array 130 when viewed from above (in the irradiation direction of X-rays).

As illustrated in FIG. 8, even when the scintillator array 130 has been correctly aligned on the APD array 120, local positional displacement may occur due to a thinned partition wall layer. In the example illustrated in FIG. 8, a scintillator pixel 131*e* has expanded downward in one of the slice directions, a scintillator pixel 131*f* has moved downward, and a scintillator pixel 131*g* has contracted downward.

In this case, the control circuitry 125 sets active areas 122*e*, 122*f*, and 122*g* so as to deal with positional displacement of the scintillator pixels 131*e*, 131*f*, and 131*g*. Specifically, the control circuitry 125 sets, as the active areas 122*e*, 122*f*, and 122*g*, the SPADs 121 included, at a predetermined number, in a range corresponding to each of the scintillator pixels 131*e*, 131*f*, and 131*g*. Note that, since it is possible to achieve the switch control for setting the active areas 122*e*, 122*f*, and 122*g* with a similar or identical method to the method described in the above embodiment, its description is omitted.

As described above, the control circuitry 125 according to the first modification of the embodiment is also able to reduce the negative effects of local positional displacement that occurs due to a thinned partition wall layer.

Second Modification

Furthermore, for example, depending on how the scintillator pixels 131 are processed, the amount of luminescence may vary due to the size of each of the elements and the surface roughness of each of the elements. In such a case, the control circuitry 125 is able to adjust a light-receiving dimension (a dimension of each of the active areas 122) in accordance with variations among the elements.

That is, the control circuitry 125 is configured to adjust the light-receiving dimension of each of the APD arrays 120, which correspond to the respective scintillator pixels 131, on the basis of a difference in an amount of luminescence in each of the scintillator pixels 131. For example, the control circuitry 125 is configured to increase the light-receiving dimension as the amount of luminescence increases.

Figure 9:
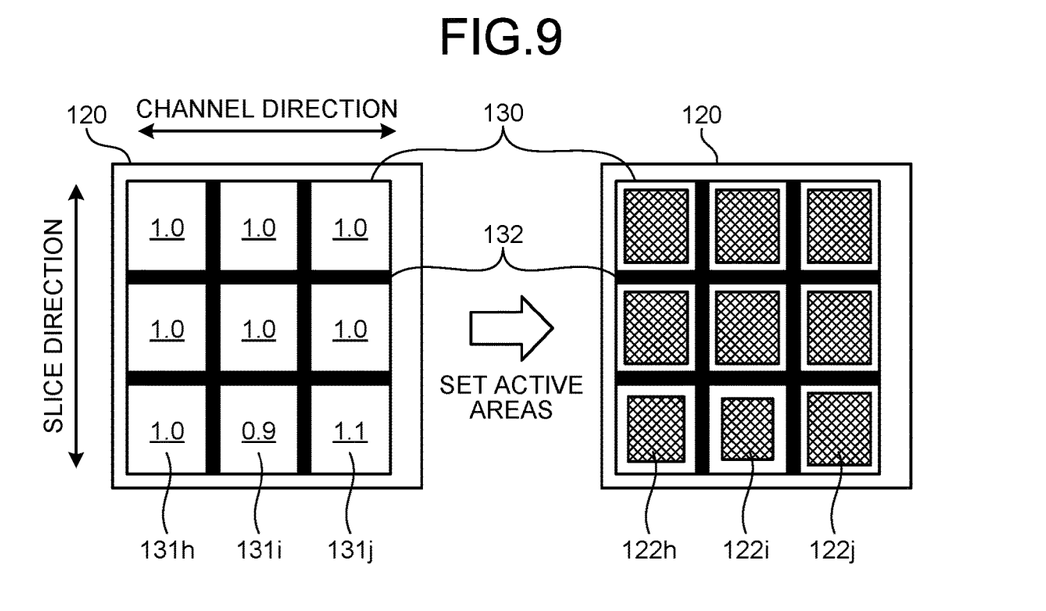
FIG. 9 is a view for describing how to set active areas according to a second modification of the embodiment.

How to set active areas according to a second modification of the embodiment will now be described with reference to FIG. 9. FIG. 9 is a view for describing how to set active areas according to the second modification of the embodiment. FIG. 9 illustrates an example of the APD array 120 and the scintillator array 130 when viewed from above (in the irradiation direction of X-rays). Note that, in FIG. 9, a numerical value illustrated in each of the scintillator pixels 131 is a relative value of the amount of luminescence of each of the scintillator pixels 131.

As illustrated in FIG. 9, the amount of luminescence of each of the scintillator pixels 131 may vary. In the example illustrated in FIG. 9, when the amount of luminescence of a scintillator pixel 131*h* is set to "1.0", the amount of luminescence of a scintillator pixel 131*i* is "0.9", while the amount of luminescence of a scintillator pixel 131*j* is "1.1".

In this case, the control circuitry 125 adjusts the dimensions of active areas 122*h*, 122*i*, and 122*j*, respectively, in accordance with the amounts of luminescence of the scintillator pixels 131*h*, 131*i*, and 131*j*. Specifically, the control circuitry 125 reduces the dimension of the active area 122*i* corresponding to the scintillator pixel 131*i* where the amount of luminescence is smaller, while increasing the dimension of the active area 122*j* corresponding to the scintillator pixel 131*j* where the amount of luminescence is greater. Note that, since it is possible to achieve the method of adjusting the dimensions of the active areas 122 with the switch control described in the above embodiment, its description is omitted.

As described above, the control circuitry 125 according to the second modification of the embodiment is able to adjust the light-receiving dimension (the dimension of each of the active areas 122) in accordance with variations among the elements.

Third Modification

Furthermore, even when positional displacement occurs, it is possible to virtually reconfigure the active areas 122 aligned correctly. That is, the control circuitry 125 is configured to virtually reconfigure light-receiving positions arrayed correctly on the basis of the respective positions of the scintillator pixels 131.

Figure 10:
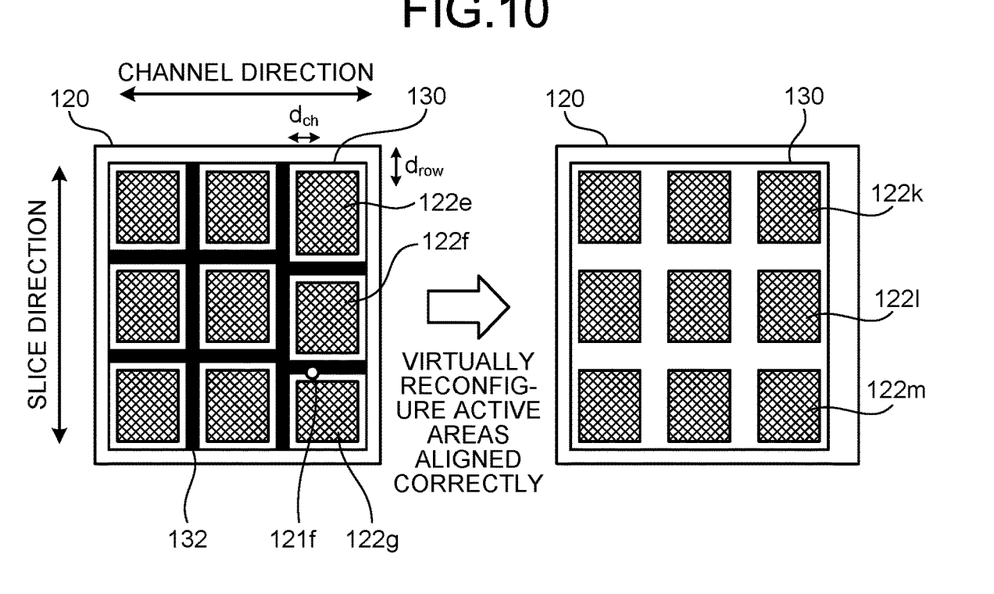
FIG. 10 is a view for describing how to set active areas according to a third modification of the embodiment.

How to set active areas according to a third modification of the embodiment will now be described with reference to FIG. 10. FIG. 10 is a view for describing how to set active areas according to the third modification of the embodiment. FIG. 10 illustrates an example of the APD array 120 and the scintillator array 130 when viewed from above (in the irradiation direction of X-rays). Note that FIG. 10 describes a case where the active areas 122*e*, 122*f*, and 122*g* set in FIG. 8 are virtually reconfigured to the active areas 122 aligned correctly.

As illustrated in FIG. 10, for example, the control circuitry 125 acquires an amount of displacement ($d_{ch}$, $d_{row}$) of each of the active areas 122. The amount of displacement represents a degree of positional displacement from a desired reference point (standard position). Then, the control circuitry 125 uses outputs of the SPADs 121 lying on a peripheral area to perform interpolation and/or extrapolation on the basis of the amounts of displacement to perform corrections to outputs when alignment has been correctly performed. Specifically, the control circuitry 125 performs interpolation and/or extrapolation on the basis of the respective amounts of displacement ($d_{ch}$, $d_{row}$) of the active areas 122e, 122f, and 122g and output signals of the SPADs 121 lying on the peripheral area to virtually reconfigure active areas 122k, 122l, and 122m aligned correctly.

In a specific example, a SPAD 121f lies near to the partition wall layer 132, and thus outputs almost no signal. However, an upper part of the SPAD 121f is supposed to be actually irradiated with X-rays. Then, the control circuitry 125 virtually calculates, through interpolation and/or extrapolation using the outputs of the SPADs 121 lying around the SPAD 121f, a signal value in accordance with the X-rays with which the upper part of the SPAD 121f is irradiated. Note that it is preferable that the SPADs 121 lying at a predetermined distance or shorter from a position at which a virtual signal value is to be calculated and lying away from the partition wall layer 132 be selected as the SPADs 121 lying on a peripheral area.

As described above, the control circuitry 125 according to the third modification of the embodiment is able to virtually reconfigure the active areas 122 aligned correctly.

Fourth Modification

Furthermore, although the above embodiment has described the case where scintillator blocks larger than the SPADs are utilized as the scintillator pixels 131, the embodiment is not limited to the case. For example, by applying optical waveguide scintillators as the scintillator arrays 130, it is possible to achieve a high-resolution, highly sensitive X-ray detector.

That is, each of the scintillator arrays 130 is an optical waveguide scintillator. In this case, the scintillator pixels 131 respectively correspond to a plurality of waveguides that the optical waveguide scintillator includes. Furthermore, it is preferable that the scintillator pixels 131 be provided, on a one-by-one basis, to the SPADs 121.

Figure 11:
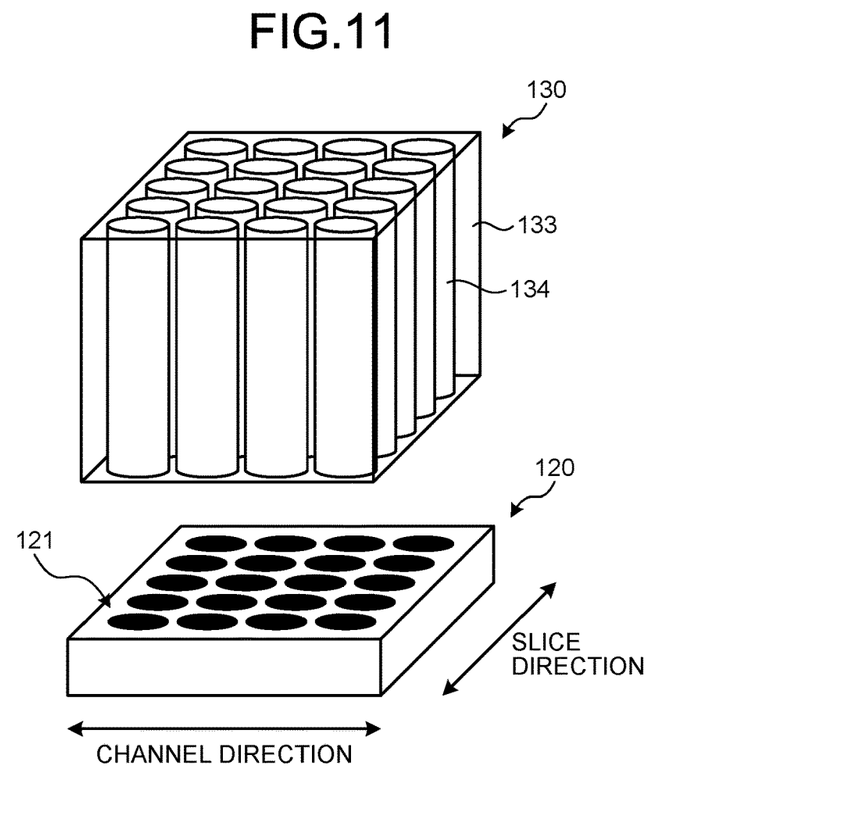
FIG. 11 is a view illustrating a configuration example of a scintillator array according to a fourth modification of the embodiment.

A configuration example of the scintillator array 130 according to a fourth modification of the embodiment will now be described with reference to FIG. 11. FIG. 11 is a view illustrating the configuration example of the scintillator array 130 according to the fourth modification of the embodiment.

As illustrated in FIG. 11, the scintillator array 130 includes a eutectic body structure where a matrix phase 133 includes a plurality of rod phases 134. The rod phases 134 are each formed into a rod shape (fiber shape) having a micrometer-order diameter, and are arrayed into a grid.

Note herein that the eutectic body structure is formed when, for example, unidirectional solidification occurs from a melt at a eutectic point where two types or more of the chemical compound scintillators is deposited simultaneously. That is, the chemical compound scintillators are those where the matrix phase 133 and each of the rod phases 134 have refraction factors different from each other. Therefore, the rod phases 134 function as "waveguides" guiding, in one direction, scintillation light generated when radiation is emitted.

In the example illustrated in FIG. 11, the rod phases 134 and the SPADs 121 are disposed to correspond to each other on a one-by-one basis. That is, the rod phases 134 respectively correspond to scintillator pixels. As a result, it is possible to achieve the scintillator array 130 having high resolution (resolving power).

Note that, although FIG. 11 has described the case where the rod phases 134 and the SPADs 121 are arrayed to correspond to each other on a one-by-one basis, the embodiment is not limited to the case. For example, the SPADs 121 may be arrayed to correspond to the one rod phase 134.

As described above, by applying optical waveguide scintillators respectively to the scintillator arrays 130 according to the fourth modification of the embodiment, it is possible to achieve a high-resolution, highly sensitive X-ray detector.

Fifth Modification

Furthermore, although the above embodiment has described the case where the positional relation between the APD array 120 and the scintillator array 130 is estimated on the basis of the intensity of an output signal of each of the SPADs 121, the embodiment is not limited to the case. For example, it is possible to estimate the positional relation between the APD array 120 and the scintillator array 130 on the basis of a count value in each of the SPADs 121.

That is, for example, when the X-ray detector 12 is inspected, the X-ray detector 12 is irradiated with X-rays to allow the control circuitry 125 to collect a count value in each of the SPADs 121. Then, the control circuitry 125 controls the switches 123 on the basis of the count value acquired in each of the SPADs 121.

For example, the control circuitry 125 changes coupling patterns for the switches 123 to collect a count value in each of the SPADs 121 in each of the coupling patterns. Then, the control circuitry 125 compares the count values respectively acquired in the SPADs 121 in the respective coupling patterns to estimate the positions of the scintillator pixels 131 and the partition wall layer 132. Then, the control circuitry 125 performs the switch control to bundle outputs of the SPADs 121 included, at a predetermined number, in a range corresponding to each of the scintillator pixels 131.

Other Embodiments

Embodiments may be implemented in other various types of forms, other than the embodiment described above.

For example, the components of the devices are functionally and schematically illustrated, and may not be necessarily physically configured as illustrated. That is, a specific, dispersed or integrated form of the devices is not limited to the forms illustrated. The devices may be wholly or partially and functionally or physically configured in a dispersed or integrated manner in desired units in accordance with various kinds of loads and use situations, for example. Furthermore, the processing functions implemented in the devices may be wholly or partially achieved as desired through a CPU and a computer program analyzed and executed by the CPU, or achieved as wired logic hardware.

Furthermore, among the steps of the processing in the embodiments and modifications, it is possible to execute manually some or all of the steps of the processing that has been described as executed automatically. Otherwise, it is possible to execute automatically, with a known method, some or all of the steps of the processing that has been described as executed manually. In addition, unless otherwise specifically described, it is possible to alter as desired the steps of processing and controls, specific names, and information including various types of data and parameters described above in the specification and the accompanying drawings.

The above-described control methods according to the embodiment and modifications can be achieved by causing a computer, such as a personal computer or a workstation, to execute a control program prepared beforehand. The control program can be distributed via a network such as the Internet. The control program can be recorded in a computer readable, non-transitory recording medium such as a hard disk, a flexible disk (FD), a compact disc read only memory (CD-ROM), a magneto-optical disk (MO), or a digital versatile disc (DVD) to allow a computer to read and execute the control program from the recording medium.

According to at least one of the embodiments described above, it is possible to improve a reduction in yield due to misalignment in a scintillator array.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A radiation detector comprising:
   a scintillator array including a plurality of scintillator pixels each configured to convert radiation into light;
   a sensor array including a plurality of detection elements each configured to detect the light;
   electronic circuitry configured to output digital data based on signals output from the detection elements;
   a switch provided between the sensor array and the electronic circuitry; and
   control circuitry configured to control the switch based on a positional relation between the sensor array and the scintillator array.

2. The radiation detector according to claim 1, wherein the switch is provided, on a one-by-one basis, to a group of the detection elements, the group including the detection elements at a predetermined number, among the detection elements.

3. The radiation detector according to claim 1, wherein the control circuitry is configured to control the switch to allow the detection elements included in a range corresponding to each of the scintillator pixels to be substantially uniform in number.

4. The radiation detector according to claim 1, wherein the control circuitry is configured to adjust a light-receiving position of the sensor array corresponding to some scintillator pixels based on positional displacement of some scintillator pixels among the scintillator pixels.

5. The radiation detector according to claim 1, wherein the control circuitry is configured to adjust a light-receiving dimension of the sensor array corresponding to each of the scintillator pixels based on a difference in an amount of luminescence in each of the scintillator pixels.

6. The radiation detector according to claim 5, wherein the control circuitry is configured to increase the light-receiving dimension as the amount of luminescence increases.

7. The radiation detector according to claim 1, wherein the control circuitry is configured to virtually reconfigure a light-receiving position arrayed correctly based on a position of each of the scintillator pixels.

8. The radiation detector according to claim 2, wherein the control circuitry is configured to control the switch based on intensity of an output signal acquired from each of the detection elements irradiated with the radiation.

9. The radiation detector according to claim 2, wherein the control circuitry is configured to control the switch based on a count value acquired in each of the detection elements irradiated with the radiation.

10. The radiation detector according to claim 1, wherein the scintillator array is an optical waveguide scintillator.

11. The radiation detector according to claim 10, wherein each of the scintillator pixels corresponds to each of a plurality of waveguides that the optical waveguide scintillator includes.

12. The radiation detector according to claim 11, wherein the scintillator pixels are respectively provided, on a one-by-one basis, to the detection elements.

* * * * *